US 8,344,072 B2

(12) United States Patent
Haering et al.

(10) Patent No.: US 8,344,072 B2
(45) Date of Patent: Jan. 1, 2013

(54) ENZYMATIC PREPARATION OF (METH)ACRYLIC ESTERS

(75) Inventors: Dietmar Haering, Schriesheim (DE); Uwe Meisenburg, Mannheim (DE); Bernhard Hauer, Fussgoenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1492 days.

(21) Appl. No.: 11/169,773

(22) Filed: Jun. 30, 2005

(65) Prior Publication Data

US 2006/0009589 A1  Jan. 12, 2006

Related U.S. Application Data

(60) Provisional application No. 60/679,662, filed on May 11, 2005.

(30) Foreign Application Priority Data

Jul. 9, 2004 (DE) .......................... 10 2004 033 555

(51) Int. Cl.
*C08F 8/14* (2006.01)
*C08L 33/00* (2006.01)
(52) U.S. Cl. ..................................... 525/330.1; 525/418
(58) Field of Classification Search .................. 560/205, 560/217, 224
See application file for complete search history.

(56) References Cited

U.S. PATENT DOCUMENTS 5,240,835 A   8/1993 Pettrone et al.
6,268,521 B1  7/2001 Gruning et al.

FOREIGN PATENT DOCUMENTS

| EP | 594109 A1 * | 4/1994 |
| EP | 0 675 141 A1 | 10/1995 |
| EP | 0 999 229 A1 | 5/2000 |
| WO | WO 03/042227 A2 | 5/2003 |
| WO | WO 2004/048585 A2 | 6/2004 |

OTHER PUBLICATIONS

Rajesh Kumar, et al., "Biocatalytic Route to Well-Defined Macromers Built around a Sugar Core." Journal of the American Chemical Society, 2002, vol. 124, 2002, pp. 1850-1851.
A.T.J.W. De Goede, et al., "Selective Lipase-Catalyzed Esterification of Alkyl Glycosides." Biocatalysis, vol. 9, 1994, pp. 145-155.
Adam B. Hajjar, et al., "Preparation of Monomeric Acrylic Ester Intermediates Using Lipase Catalysed Transesterifications in Organic Solvents." Biotechnology Letters, vol. 12, No. 11, 1990, pp. 825-830.

* cited by examiner

*Primary Examiner* — Kamal Saeed
(74) *Attorney, Agent, or Firm* — Oblon, Spivak, McClelland, Maier & Neustadt, L.L.P.

(57) ABSTRACT

Process for preparing partial (meth)acrylic esters of polyalcohols having different hydroxyl groups, process for their preparation, and use thereof.

11 Claims, No Drawings

ENZYMATIC PREPARATION OF (METH)ACRYLIC ESTERS

The present invention relates to a process for preparing partial (meth)acrylic esters of polyalcohols having different hydroxyl groups, to processes for their preparation, and to the use thereof.

(Meth)acrylic esters are generally prepared by acid- or base-catalyzed esterification of (meth)acrylic acid or transesterification of other (meth)acrylic esters with alcohols.

Partial (meth)acrylic esters of polyalcohols containing different hydroxyl groups generally cannot be prepared specifically by an esterification or transesterification, since statistical mixtures are obtained.

In the case of base-catalyzed transesterification or other syntheses the products are often complex mixtures, occasionally colored. In order to remove coloration and unconverted reactants it is necessary to work up the product mixtures by means of costly and inconvenient alkaline washes.

The unpublished German patent application with the file reference 10308504.1 discloses a process for preparing partially acrylated polyols by protecting OH groups using acetal or ketal groups, enzymatically (meth)acrylating the free OH groups and subsequently deprotecting the protective groups, if appropriate.

A disadvantage of this process is that additional steps are needed for the introduction and removal of the protective groups.

The preparation of (meth)acrylic esters by an enzymatic esterification or transesterification is known.

Kumar and Gross describe in J. Am. Chem. Soc. 2002, 124, 1850-1851 the lipase-catalyzed reaction of isopropylidene-protected sugars by reaction with vinyl meth-acrylate. Complete reaction is achieved by means of the specific reactant, vinyl methacrylate, since vinyl alcohol liberated is withdrawn from the reaction equilibrium as acetaldehyde. A disadvantage of this process is that vinyl methacrylate, as a specialty monomer, is expensive and is commercially available only in small quantities.

A. T. J. W. de Goede et al. describe in Biocatalysis, 1994, 9, 145-155 the transesterification of α-O-octylglucoside with ethyl acrylate to form the 6-O-acrylic ester in the presence of lipases. Disadvantages of this process are that it is restricted to glucosides and glycosidic bonds and reacts sensitively to steric influences in the glucoside. Moreover, products with relatively high degrees of acrylation are obtained due to unselective side reactions.

EP-A1 999 229 describes the enzymatic esterification and transesterification of polyoxyalkylenes with (meth)acrylic acid and (meth)acrylic esters.

WO 03/042227 discloses the lipase-catalyzed transesterification of alkyl acrylates with sugars.

Hajar et al. describe in Biotechnol. Lett. 1990, 12, 825-830 the enzymatic transesterification of cyclic and open-chain alkanediols with ethyl acrylate with a lipase from Chromobacterium viscosum. The reactions proceed with an 18-fold molar excess of the alkyl acrylate over the diol in a solvent-free system. This produces mixtures of monoacrylates and diacrylates.

In that reaction 5 mmol of diol in each case were reacted in 10 ml of ethyl acrylate (92 mmol) with 100 mg of lipase from Chromobacterium viscosum at 30° C.

In the acrylation of diols containing two primary OH groups (e.g., 1,6-hexanediol) the diol had undergone >95% reaction after 7 d. The result was a mixture of monoacrylates and diacrylates, containing >80% of diacrylate depending on reaction time.

In the acrylation of diols having two secondary OH groups (e.g., 2,5-hexanediol) the reaction time was much higher: even after 14 days the diol had undergone only about 50% reaction. The result was an acrylate mixture composed of monoacrylates and diacrylates, containing 70% of monoacrylate and 30% of diacrylate.

In the case of the acrylation of diols containing one primary and one secondary OH group (e.g., 1,2-hexanediol) the diol had undergone reaction to an extent of about 85% only after 7 d. The result was a mixture of monoacrylates and diacrylates, which after 14 days' reaction time contained 5% of diacrylate. The diacrylate content rose continuously in the course of the reaction period.

Accordingly it is not possible under these reaction conditions to obtain sufficient selectivity of monoacrylation to diacrylation product; all that is found is the usual, moderate selectivity between primary and secondary alcohol groups.

U.S. Pat. No. 5,240,835 describes the transesterification of alkyl acrylates with alcohols under catalysis by a biocatalyst from Corynebacterium oxydans. Exemplified therein is the reaction of a 96-fold molar excess of ethyl acrylate with 2,2-dimethyl-1,3-propanediol. The yield, after 3 days at 30° C., was only 21%.

Athawale and Manjrekar (Tetrahedron Lett. 2001, 42, 4541-4543) describe the lipase-catalyzed acrylation of alkaloids using 2,3-butanedione monooxime acrylate. The monomer was polymerized and used for inducing enantioselective Michael addition.

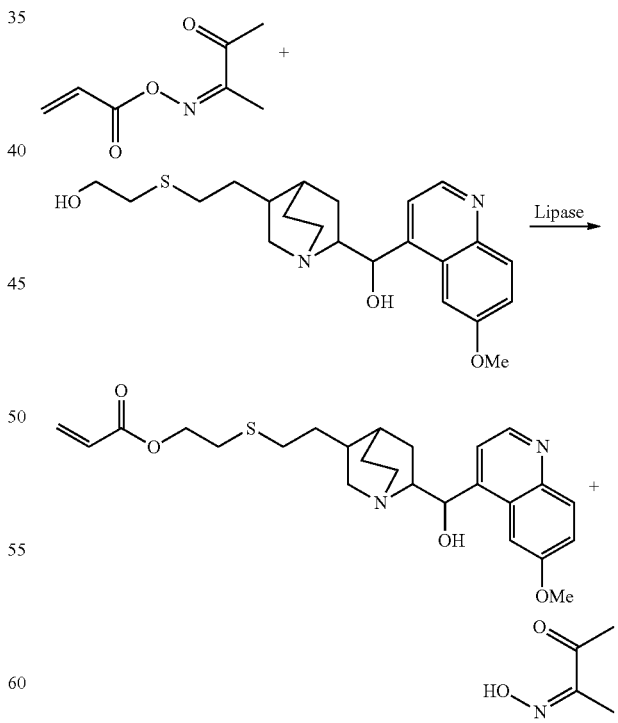

Athawale and Gaonkar (Macromolecules 1999, 32, 6065-6068) describe the lipase-catalyzed acrylation of 2-phenylethanols using 2,3-butanedione monooxime acrylate. The monomer was subsequently polymerized.

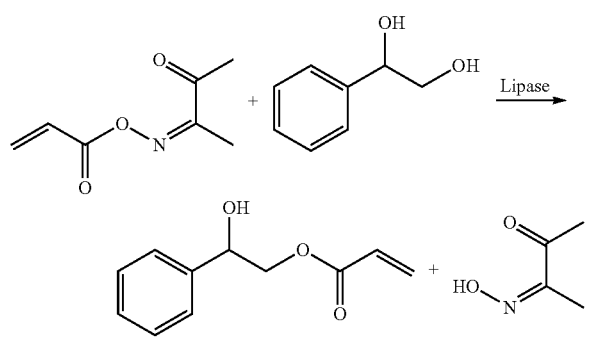

Ghogare and Kumar (J. Chem. Soc. 1989, 1533-1535) describe the lipase-catalyzed acrylation of various alcohols, including 2-ethylhexane-1,3-diol, with an activated 2,3-butanedione monooxime acrylate.

A disadvantage of these reactions is the need to use activated acrylates, which are expensive and difficult to acquire industrially.

It was an object of the present invention to provide a process with which partial (meth)acrylic esters of polyalcohols having different hydroxyl groups can be prepared in high conversions with high selectivities in respect of the reaction of the different hydroxyl groups and of high purities, from simple reactants. The synthesis ought to proceed under mild conditions, giving products having a low color number and high purity. Moreover there should be no need for protective groups, and nor should it be necessary to use activated (meth)acrylic acid derivatives, such as monooximes or vinyl (meth)acrylate, for example.

This object has been achieved by means of a process for preparing partial (meth)acrylic esters (F) of at least dihydric polyalcohols (C) containing different hydroxyl groups, which comprises subjecting alternatively (1) at least one polyalcohol ($C_1$) having at least one primary hydroxyl group and at least one secondary hydroxyl group, or (2) at least one polyalcohol ($C_2$) having at least one primary hydroxyl group and at least one tertiary hydroxyl group, or (3) at least one polyalcohol ($C_3$) having at least one secondary hydroxyl group and at least one tertiary hydroxyl group, the more highly substituted hydroxyl group carrying in the β position at least one alkyl, cycloalkyl, aryl or aralkyl radical, or (4) at least one polyalcohol ($C_4$) having at least two primary hydroxyl groups, of which at least one carries in the β position at least one alkyl, cycloalkyl, aryl or aralkyl radical and at least one carries in the β position no such radical, or (5) at least one polyalcohol ($C_5$) having at least two secondary hydroxyl groups, of which at least one carries in the β position at least one alkyl, cycloalkyl, aryl or aralkyl radical and at least one carries in the β position no such radical, to esterification with (meth)acrylic acid or to transesterification with at least one (meth)acrylic ester (D) in the presence of at least one enzyme (E).

By means of the process of the invention it is possible to produce partial (meth)acrylic esters (F) in high chemical and space/time yield under mild conditions with good color numbers, with no need for protective-group operations, and using simple starting materials.

(Meth)acrylic acid in this text stands for methacrylic acid and acrylic acid, preferably for acrylic acid.

Polyalcohols (C) suitable in accordance with the invention are at least dihydric alcohols, preferably dihydric to decahydric, more preferably dihydric to hexahydric, very preferably dihydric to tetrahydric, in particular dihydric to trihydric, and especially dihydric alcohols.

These inventively suitable polyalcohols (C) carry differentiable hydroxyl groups: that is, in accordance with the invention they possess, in the same molecule, at least one lower-substituted hydroxyl group and at least one higher-substituted hydroxyl group. As a result of the different environment of the hydroxyl groups they are differentiable in an enzymatic (meth)acrylation, so that in accordance with the process of the invention a higher selectivity is attained than with the prior art processes.

By lower- and higher-substituted is meant the number of substituents on the carbon atom to which the respective hydroxyl group is attached, in other words on the a carbon atom (see below).

Lower-substituted hydroxyl groups are, for example, primary or secondary hydroxyl groups, while higher-substituted hydroxyl groups are, for example, secondary or tertiary hydroxyl groups. The degree of substitution relates to the number of non-hydrogen atoms connected to the carbon atom that is connected to the hydroxyl group under consideration.

The polyalcohols (C) contain at least one lower-substituted hydroxyl group, preferably 1 to 6, more preferably 1 to 4, very preferably 1 to 3, in particular 1 or 2, and especially one, and also at least one higher-substituted hydroxyl group, preferably 1 to 6, more preferably 1 to 4, very preferably 1 to 3, in particular 1 or 2, and especially one.

An additional feature in accordance with the invention is the presence of at least one alkyl, cycloalkyl, aryl or aralkyl radical in the β position with respect to the higher-substituted hydroxyl group, preference being given to at least one alkyl, cycloalkyl, aryl or aralkyl radical in the β position.

The general convention here is that the carbon atom to which the hydroxyl group in question is joined is the a carbon atom, the next one along is the β carbon atom, which is followed in turn by the γ carbon atom, as depicted schematically, for example, in the following diagram (which does not show any possible substituents):

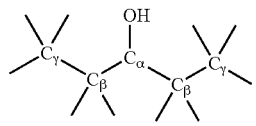

Preferred polyalcohols are alternatively (1) polyalcohols ($C_1$) having at least one primary hydroxyl group and at least one secondary hydroxyl group, or (2) polyalcohols ($C_2$) having at least one primary hydroxyl group and at least one tertiary hydroxyl group, or (3) polyalcohols ($C_3$) having at least one secondary hydroxyl group and at least one tertiary hydroxyl group, or (4) polyalcohols ($C_4$) having at least two primary hydroxyl groups, of which at least one carries in the β position at least one alkyl, cycloalkyl, aryl or aralkyl radical and at least one carries in the β position no such radical, or (5) polyalcohols ($C_5$) having at least two secondary hydroxyl groups, of which at least one carries in the β position at least one alkyl, cycloalkyl, aryl or aralkyl radical and at least one carries in the β position no such radical.

Among these polyalcohols, particular preference is given to polyalcohols ($C_1$) and ($C_2$) and very particular preference to polyalcohols ($C_1$).

Particular preference is given to polyalcohols (C) of the formula I

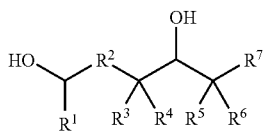

and formula II

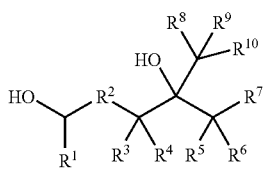

and formula III

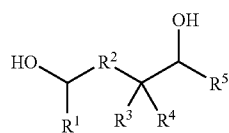

in which $R^1$ and $R^3$ to $R^{10}$ each independently of one another are hydrogen, $C_1$-$C_{18}$ alkyl, $C_2$-$C_{18}$ alkyl optionally interrupted by one or more oxygen and/or sulfur atoms and/or one or more substituted or unsubstituted imino groups, or are $C_6$-$C_{12}$ aryl, $C_5$-$C_{12}$ cycloalkyl or a five- or six-membered, oxygen-, nitrogen- and/or sulfur-containing heterocycle, it being possible for the specified radicals to be substituted in each case by aryl, alkyl, aryloxy, alkyloxy, heteroatoms and/or heterocycles, and $R^2$ is a single bond, $C_1$-$C_{20}$ alkylene, $C_5$-$C_{12}$ cycloalkylene, $C_6$-$C_{12}$ arylene or $C_2$-$C_{20}$ alkylene which is interrupted by one or more oxygen and/or sulfur atoms and/or one or more substituted or unsubstituted imino groups and/or one or more cycloalkyl, —(CO)—, —O(CO)O—, —(NH)(CO)O—, —O(CO)(NH)—, —O(CO)— or —(CO)O— groups, it being possible for the specified radicals to be substituted in each case by aryl, alkyl, aryloxy, alkyloxy, heteroatoms and/or heterocycles, where for the case (1) in formula I $R^1$ is hydrogen and at least one of the radicals $R^3$ to $R^7$ is other than hydrogen, for the case (2) in formula II $R^1$ is hydrogen and at least one of the radicals $R^3$ to $R^{10}$ is other than hydrogen, and for the case (3) in formula II $R^1$ is other than hydrogen and at least one of the radicals $R^3$ to $R^{10}$ is other than hydrogen, for the case (4) in formula III $R^1$ and $R^5$ are hydrogen and at least one of the radicals $R^3$ and $R^4$ is other than hydrogen, and for the case (5) in formula III $R^1$ and $R^5$ are other than hydrogen and at least one of the radicals $R^3$ and $R^4$ is other than hydrogen.

The radicals $R^1$ to $R^{10}$ preferably contain no other hydroxyl and/or amino groups; with particular preference the radicals $R^1$ to $R^{10}$ contain no hydroxyl and/or amino and/or ester and/or amide groups and with very particular preference the radicals $R^1$ to $R^{10}$ contain no further oxygen and/or nitrogen atoms.

With particular preference the radicals $R^1$ and $R^3$ to $R^{10}$ are hydrogen or hydrocarbons, i.e., they comprise exclusively carbon and hydrogen.

With particular preference the radical $R^2$ and $R^3$ to $R^{10}$ is in each case a single bond or a hydrocarbon.

In the above definitions $C_1$-$C_{20}$ alkylene optionally substituted by aryl, alkyl, aryloxy, alkyloxy, heteroatoms and/or heterocycles is for example methylene, 1,1-ethylene, 1,2-ethylene, 1,1-propylene, 1,2-propylene, 1,3-propylene, 1,1-butylene, 1,2-butylene, 1,3-butylene, 1,4-butylene, 1,6-hexylene, 2-methyl-1,3-propylene, 2-ethyl-1,3-propylene, 2,2-dimethyl-1,3-propylene, or 2,2-dimethyl-1,4-butylene, $C_5$-$C_{12}$ cycloalkylene optionally substituted by aryl, alkyl, aryloxy, alkyloxy, heteroatoms and/or heterocycles is for example cyclopropylene, cyclopentylene, cyclohexylene, cyclooctylene, or cyclododecylene, $C_2$-$C_{20}$ alkylene optionally substituted by aryl, alkyl, aryloxy, alkyloxy, heteroatoms and/or heterocycles and optionally interrupted by one or more oxygen and/or sulfur atoms and/or one or more substituted or unsubstituted imino groups and/or one or more cycloalkyl, —(CO)—, —O(CO)O—, —(NH)(CO)O—, —O(CO)(NH)—, —O(CO)— or —(CO)O— groups is for example 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3-enylene, 1-oxa-1,5-pent-3-ynylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1,7-heptylene, 4-aza-1-oxa-1,6-hexylene, 1-aza-4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1,7-dioxa-4-(2'-hydroxyethyl)-1,7-heptylene, 4-aza-1-oxa-(2'-hydroxyethyl)-1,6-hexylene or 1,4-piperazinylene, $C_6$-$C_{12}$ arylene optionally substituted by aryl, alkyl, aryloxy, alkyloxy, heteroatoms and/or heterocycles is for example 1,2-, 1,3- or 1,4-phenylene, 4,4'-biphenylene, tolylene or xylylene, $C_1$-$C_{18}$ alkyl or $C_2$-$C_{18}$ alkyl which is optionally interrupted by one or more oxygen and/or sulfur atoms and/or one or more substituted or unsubstituted imino groups is for example methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxy-carbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxy-ethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butyl-thiomethyl, 2-dodecylthioethyl, 2-phenylthioethyl, 2,2,2-trifluoroethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and preferably methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, 2-cyanoethyl, 2-cyanopropyl, chloromethyl, 2-chloroethyl, trichloromethyl, trifluoromethyl, 1,1-dimethyl-2-chloroethyl and 2,2,2-trifluoroethyl, $C_8$-$C_{12}$ aryl optionally interrupted by one or more oxygen and/or sulfur atoms and/or one or more substituted or unsubstituted imino groups is for example phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, and preferably phenyl, tolyl, xylyl, α-naphthyl, p-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, chloronaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, $C_5$-$C_{12}$ cycloalkyl optionally interrupted by one or more oxygen and/or sulfur atoms and/or by one or more substituted or unsubstituted imino groups is for example cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl and also a saturated or unsaturated bicyclic system such as norbornyl or norbornenyl, for example, and preferably cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, chlorocyclohexyl, dichlorocyclohexyl, or dichlorocyclopentyl and also a saturated or unsaturated bicyclic system such as norbornyl or norbornenyl, for example, and a five- or six-membered, oxygen-, nitrogen- and/or sulfur-containing heterocycle optionally interrupted by one or more oxygen and/or sulfur atoms and/or by one or more substituted or unsubstituted imino groups is for example furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

Examples of $R^2$ are a single bond, methylene, 1,1-ethylene, 1,2-ethylene, 1,1-propylene, 1,2-propylene, 1,3-propylene, 1,1-dimethyl-1,2-ethylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 3-methyl-1,5-pentylene, 3,5-heptylene, 1,2-cyclopentylene, 1,3-cyclopentylene, 1,2-cyclohexylene, 1,3-cyclohexylene and ortho-phenylene, preferably a single bond, methylene, 1,1-ethylene, 1,2-ethylene, 1,1-propylene, 1,2-propylene, 1,3-propylene, 1,1-dimethyl-1,2-ethylene and 3,5-heptylene, more preferably a single bond, methylene, 1,1-ethylene, 1,2-ethylene, 1,1-propylene, 1,3-propylene and 3,5-heptylene, and with very particular preference 1,1-propylene and 3,5-heptylene.

Preferred examples of $R^1$ and $R^3$ to $R^{10}$ are independently of one another hydrogen, $C_1$-$C_4$ alkyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, naphthyl or benzyl.

$C_1$-$C_4$ alkyl for the purposes of this text denotes methyl, ethyl, isopropyl, n-propyl, n-butyl, isobutyl, sec-butyl or tert-butyl, preferably methyl, ethyl, n-propyl and n-butyl, more preferably methyl, ethyl and n-butyl, and very preferably methyl and ethyl.

Preferred examples of polyalcohols (C) are 2-ethyl-1,3-hexanediol, 2-methyl-1,3-pentanediol, 2-propyl-1,3-heptanediol, 2,4-diethyloctane-1,5-diol, 2,2-dimethyl-1-phenyl-1,3-propanediol, 2-methyl-1,5-pentanediol, 3-methyl-2,6-heptanediol, 4-methylcyclohexane-1,3-diol and 3,3-dimethyl-1,2-butanediol. Particular preference is given to 2-ethyl-1,3-hexanediol, 2-methyl-1,3-pentanediol and 2,4-diethyloctane-1,5-diol, and very particular preference to 2-ethyl-1,3-hexanediol and 2,4-diethyloctane-1,5-diol.

As regards the differentiability of the hydroxyl groups it is necessary in accordance with the invention for the hydroxyl groups to have a different environment: that is, for example, not to have a mirror plane (σ), as is the case for example with 2-methyl-1,3-propanediol, and/or not to have a $C_2$ and/or $C_3$ axis of rotation, such as in the case of 2,2-dimethyl-1,3-propanediol or trimethylolethane, for example.

The reaction step is the esterification with (meth)acrylic acid or, preferably, the transesterification of the polyalcohol (C) with at least one, preferably one, (meth)acrylate (D) in the presence of at least one, preferably one, enzyme (E) that catalyzes the transesterification.

Compounds (D) can be (meth)acrylic acid or esters of (meth)acrylic acid with a saturated alcohol, preferably saturated $C_1$-$C_{10}$ alkyl esters or $C_3$-$C_{12}$ cycloalkyl esters of (meth)acrylic acid, more preferably saturated $C_1$-$C_4$ alkyl esters of (meth)acrylic acid.

Saturated for the purposes of this text means compounds without multiple C—C bonds (except of course for the C=C double bond in the (meth)acrylic units).

Examples of compounds (D) are methyl, ethyl, n-butyl, isobutyl, n-octyl, and 2-ethylhexyl(meth)acrylate, 1,2-ethylene glycol di- and mono(meth)acrylate, 1,4-butanediol di- and mono(meth)acrylate, 1,6-hexanediol di- and mono (meth)acrylate, trimethylolpropane tri(meth)acrylate, and pentaerythritol tetra(meth)acrylate.

Particular preference is given to methyl, ethyl, n-butyl, and 2-ethylhexyl(meth)acrylate and very particular preference to methyl, ethyl, and n-butyl(meth)acrylate.

Where the aforementioned alcohols are optically active, they are used preferably in racemic form or as diastereomer mixtures; it is, however, also possible to use them as pure enantiomers or diastereomers, or as enantiomer mixtures.

The enzymatic esterification or transesterification with a (meth)acrylate takes place in general at from 0 to 100° C., preferably from 20 to 80° C., more preferably from 20 to 70° C., and very preferably from 20 to 60° C.

Examples of enzymes (E) useful in accordance with the invention are those selected from hydrolases (E.C. 3.-.-.-), and among these especially from the esterases (E.C. 3.1.-.-), lipases (E.C. 3.1.1.3), glycosylases (E.C. 3.2.-.-), and proteases (E.C. 3.4.-.-), in free form or in a form in which they are chemically or physically immobilized on a carrier, preferably lipases, esterases or proteases, and more preferably esterases (E.C. 3.1.-.-). Very particular preference is given to Novozyme 435 (lipase from *Candida antarctica* B) or lipase from *Alcaligenes* sp., *Aspergillus* sp., *Mucor* sp., *Penicillium* sp., *Geotricum* sp., *Rhizopus* sp., *Burkholderia* sp., *Candida* sp., *Pseudomonas* sp., *Thermomyces* sp., or porcine pancreas, and especial preference is to lipase from *Candida antarctica* B or from *Burkholderia* sp.

The enzyme content of the reaction medium is generally in the range from about 0.1 to 10% by weight, based on the alcohol (C) employed.

The reaction time depends among other things on the temperature, on the amount of the enzyme catalyst used and its activity, and on the required conversion, and also on the partly esterified alcohol. The reaction time is preferably adapted so that the conversion of the hydroxyl functions present in the alcohol (C) that are to be reacted, i.e., the lower-substituted hydroxyl functions, is at least 70%, preferably at least 80%, more preferably at least 90%, very preferably at least 95%, in particular at least 97%, and especially at least 98%. The time sufficient for this is generally from 1 to 72 hours, preferably from 3 to 36 hours, and more preferably from 3 to 24 hours.

The molar ratio of (meth)acrylic acid compound (D) (based on the (meth)acrylic units) to partly esterified alcohol (C) (based on hydroxyl groups) can be set within a wide range, such as in a ratio, for example, of from 100:1 to 1:1, preferably from 50:1 to 1:1, more preferably from 20:1 to 1:1, and very preferably from 10:1 to 1:1.

The reaction can proceed in organic solvents or mixtures thereof or without the addition of solvents. It is preferred not to add solvent. The batches are generally substantially free of water (i.e., less than 10%, preferably less than 5%, more preferably less than 1%, and very preferably less than 0.5% by volume of water added).

Suitable organic solvents are those known for these purposes, examples being tertiary monools, such as $C_3$-$C_6$ alcohols, preferably tert-butanol, tert-amyl alcohol, pyridine, poly-$C_1$-$C_4$ alkylene glycol di-$C_1$-$C_4$ alkyl ethers, preferably polyethylene glycol di-$C_1$-$C_4$ alkyl ethers, such as 1,2-dimethoxyethane, diethylene glycol dimethyl ether, polyethylene glycol dimethyl ether 500, methyl tert-butyl ether, ethyl tert-butyl ether, $C_1$-$C_4$ alkylene carbonates, especially propylene carbonate, $C_3$-$C_6$ alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and single-phase or multiphase mixtures thereof. It can be advantageous to separate alcohol or water that is liberated by means of a binary or ternary heteroazeotrope which boils as close as possible to the temperature optimum of the enzyme used. The alcohol removed in this way can then be removed by phase separation or membrane vapor separation.

As an option it is possible to add aqueous solvents to the organic solvents, thereby producing single-phase or multiphase reaction solutions, depending on the organic solvent. Examples of aqueous solvents are water and also aqueous, dilute (e.g., 10 to 100 mM) buffers, with a pH for example in the range from about 6 to 8, such as potassium phosphate buffer or TRIS-HCl buffer, for example.

The water fraction in the reaction mixture is generally 0-10% by volume. The reactants are preferably used without pretreatment (drying, water doping).

The substrates are either in solution, in suspension as solids, or in emulsion in the reaction medium. The initial concentration of the reactants is preferably in the range from about 0.1 to 20 mol/l, in particular from 0.15 to 10 mol/l or from 0.2 to 5 mol/l.

The reaction can take place continuously, in a tube reactor or in a stirred reactor cascade, for example, or batchwise.

The reaction can be conducted in all reactors suitable for such reactions. Reactors of this kind are known to the skilled worker. The reaction preferably takes place in a stirred tank reactor or fixed bed reactor.

The reaction mixture can be mixed using any desired methods. There is no need for special stirring apparatus. The reaction medium can be a single phase or a plurality of phases and the reactants are dissolved, suspended or emulsified therein, charged to the reaction vessel together where appropriate with the molecular sieve, and admixed with the enzyme preparation at the start of the reaction and also, where appropriate, one or more times during the course of the reacton. The temperature during the reaction is adjusted to the desired level and can, if desired, be raised or lowered during the course of the reaction.

Where the reaction is carried out in a fixed bed reactor, said reactor is preferably packed with immobilized enzymes, the reaction mixture being pumped through a column packed with the enzyme. It is also possible to carry out the reaction in a fluidized bed, in which case the enzyme is used in a form in which it is immobilized on a carrier. The reaction mixture can be pumped continuously through the column, with the residence time and hence the desired conversion being controllable by means of the flow rate. It is also possible to pump the reaction mixture in circulation through a column, with the possibility also of distillative removal of the alcohol that is liberated at the same time, under reduced pressure.

The removal of water in the case of an esterification, or of alcohols released in a transesterification from the alkyl(meth) acrylates, takes place continuously or gradually in a manner known per se, by means of reduced pressure, azeotropic removal, absorption, pervaporation, and diffusion via membranes, for example.

Suitable for this purpose are, preferably, molecular sieves or zeolites (with a pore size, for example, in the range of about 3-10 angstroms), distillative separation or separation using appropriate semipermeable membranes.

Yet another possibility is to pass the isolated mixture of alkyl(meth)acrylate and its parent alcohol, said mixture frequently forming an azeotrope, directly to a plant for the preparation of the alkyl(meth)acrylate, so as to reuse it therein in an esterification with (meth)acrylic acid.

After the end of the reaction the reaction mixture obtained from the esterification or transesterification can be used further without further purification or, if required, can be purified in a further step.

Generally in a purification step the enzyme used is just separated off from the reaction mixture and the reaction product is freed from any organic solvent used.

The enzyme is separated off generally by filtration, absorption, centrifugation or decanting. The enzyme separated off can subsequently be used for further reactions.

Removal of the organic solvent takes place generally by distillation, rectification or, in the case of solid reaction products, by filtration.

For the further purification of the reaction product it is also possible to carry out a chromatography.

Preferably in the purification step, however, just the enzyme used and any solvent used are separated off.

The reaction conditions in the enzymatic esterification or transesterification are mild. The low temperatures and other mild conditions prevent the formation of by-products during the reaction, which might otherwise originate, for example, from chemical catalysts or as a result of unwanted free-radical polymerization of the (meth)acrylate used, which can otherwise be prevented only by adding stabilizers.

In the reaction regime of the invention it is possible to add additional stabilizer to the (meth)acrylic compound (D) over and above the storage stabilizer present in any case, examples of such additional stabilizers including hydroquinone monomethyl ether, phenothiazine, phenols, such as 2-tert-butyl-4-methylphenol or 6-tert-butyl-2,4-dimethylphenol, for example, or N-oxyls, such as 4-hydroxy-2,2,6,6-tetramethyl-piperidine-N-oxyl, and 4-oxo-2,2,6,6-tetramethylpiperidine-N-oxyl, in amounts for example of from 50 to 2000 ppm. The transesterification or esterification is advantageously conducted in the presence of an oxygenous gas, preferably air or air/nitrogen mixtures.

Additionally the enzyme catalyst can be removed without problems from the end product.

If appropriate the reaction mixture can be purified if desired, purification taking place for example by filtration, distillation, rectification, chromatography, treatment with ion exchangers, adsorbents, neutral, acidic and/or alkaline washing, stripping or crystallization.

The present invention further provides the (meth)acrylates obtainable from the polyalcohols (C) having different hydroxyl groups, the only hydroxyl groups in these (meth) acrylates that have been (meth)acrylated being the lower-substituted hydroxyl groups, and not the higher-substituted hydroxyl groups.

These (meth)acrylates are preferably the compounds of the formula Ia

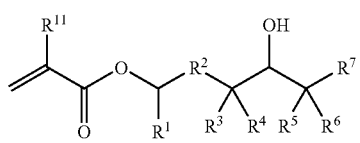

and formula IIa

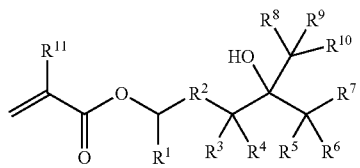

and formula IIIa

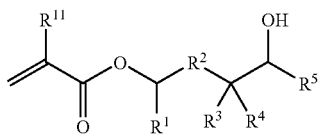

in which
$R^1$ to $R^{10}$ are as defined above and
$R^{11}$ is hydrogen or methyl.

Particular preference is given to 2-ethyl-3-hydroxyhexyl, 2-methyl-3-hydroxypentyl and 2,4-diethyl-1,5-dihydroxyoctyl(meth)acrylate, great preference to 2-ethyl-3-hydroxyhexyl acrylate, 2-methyl-3-hydroxypentyl acrylate and 2,4-diethyl-1,5-dihydroxyoctyl acrylate, especial preference to 2-ethyl-3-hydroxyhexyl acrylate and 2,4-diethyl-1,5-dihydroxyoctyl acrylate, and preference especially to 2,4-diethyl-1,5-dihydroxyoctyl acrylate.

The color number of the partial (meth)acrylic esters obtained in accordance with the invention is generally below 100 APHA in accordance with DIN ISO 6271, preferably below 80, more preferably below 60, very preferably below 40, and in particular below 20 APHA.

Coatings thus obtainable have very high scratch resistance, hardness, chemical resistance, elasticity, and adhesion, on both hydrophilic and hydrophobic substrates.

The partial (meth)acrylic esters (F) obtainable inventively can be used with advantage as monomers or comonomers in poly(meth)acrylates or as reactive diluents in thermally curable, radiation-curable and/or dual-cure poly(meth)acrylates.

Poly(meth)acrylates of this kind are suitable, for example, as binders in thermally curable, radiation-curable or dual-cure coating compositions and also in adhesives, e.g., acrylate adhesives, and also in sealants. Additionally the partial (meth) acrylic esters (F) can be used in polyurethanes, such as in PU dispersions, PU foams, PU adhesives, and PU coatings, for example. By thermally curable is meant, for example, one-component (1K) and two-component (2K) coating systems which are additionally reacted with crosslinking reagents, e.g., melamine resins or isocyanate derivatives.

The present application accordingly further provides for the use of the partial (meth)acrylic esters prepared by the process of the invention as reactive diluents or binders in radiation-curable or dual-cure coating materials, preferably in topcoats, more preferably in transparent clearcoat materials. The partial (meth)acrylic esters prepared in accordance with the invention can of course also be used as monomers in polymerizations, together where appropriate with other polymerizable monomers, such as (meth)acrylic acid, (meth) acrylic esters, styrene, butadiene, acrylonitrile, vinyl acetate, N-vinylpyrrolidone, 4-hydroxybutyl vinyl ether or N-vinylformamide, for example.

"Dual cure" means that the coating materials are curable thermally and with actinic radiation. Actinic radiation for the purposes of the present invention means electromagnetic radiation such as visible light, UV radiation or X-rays, especially UV radiation, and corpuscular radiation such as electron beams.

Radiation-curable binders are those which can be cured by means of actinic radiation as defined above, in particular by means of UV radiation.

The present invention further provides coating formulations comprising the partial (meth)acrylic esters obtainable by the process of the invention. The partial (meth)acrylic esters can be used both in basecoat and in topcoat materials. In view of their particular properties, such as the raising of the scratch resistance and elasticity, and the lowering of the viscosity, particularly in the case of branched polyacrylates, of a radiation-cured clearcoat, their use in topcoats is preferred.

Besides the partial (meth)acrylic esters (F) obtainable by the process of the invention a radiation-curable composition of the invention may also comprise the following components:

(G) at least one polymerizable compound having two or more copolymerizable, ethylenically unsaturated groups,
(H) if appropriate, reactive diluents,
(I) if appropriate, photoinitiators, and
(J) if appropriate, further, typical coatings additives.

Suitable compounds (G) include radiation-curable, free-radically polymerizable compounds having a plurality of, i.e., at least two, copolymerizable, ethylenically unsaturated groups.

Compounds (G) are preferably vinyl ether compounds or (meth)acrylate compounds, particular preference being given in each case to the acrylate compounds, i.e., to the derivatives of acrylic acid.

Preferred vinyl ether and (meth)acrylate compounds (G) contain from 2 to 20, preferably from 2 to 10, and very preferably from 2 to 6 copolymerizable, ethylenically unsaturated double bonds.

Particular preference is given to such compounds (G) having an ethylenically unsaturated double bond content of 0.1-0.7 mol/100 g, very preferably 0.2-0.6 mol/100 g.

The number-average molecular weight $M_n$ of the compounds (G), unless otherwise specified, is preferably below 15 000, more preferably 300-12 000, very preferably from 400 to 5000, and in particular 500-3000 g/mol (as determined by gel permeation chromatography using polystyrene standards and tetrahydrofuran as eluent).

As (meth)acrylate compounds mention may be made of (meth)acrylic esters and especially acrylic esters and also of vinyl ethers of polyfunctional alcohols, especially those which other than the hydroxyl groups contain no functional groups or, if any at all, contain ether groups. Examples of such alcohols include bifunctional alcohols, such as ethylene glycol, propylene glycol and their counterparts with higher degrees of condensation, such as diethylene glycol, triethylene glycol, dipropylene glycol, tripropylene glycol etc., 1,2-, 1,3- or 1,4-butanediol, 1,5-pentanediol, 1,6-hexanediol, 3-methyl-1,5-pentanediol, neopentyl glycol, alkoxylated phenolic compounds, such as ethoxylated and/or propoxylated bisphenols, 1,2-, 1,3- or 1,4-cyclohexanedimethanol, alcohols with a functionality of three or more, such as glycerol, trimethylolpropane, butanetriol, trimethylolethane, pentaerythritol, ditrimethylolpropane, dipentaerythritol, sorbitol, mannitol, and the corresponding alkoxylated alcohols, especially ethoxylated and/or propoxylated alcohols.

The alkoxylation products are obtainable conventionally by reacting the above alcohols with alkylene oxides, especially ethylene oxide or propylene oxide. The degree of alkoxylation per hydroxyl group is preferably from 0 to 10, i.e., 1 mol of hydroxyl group may have been alkoxylated with up to 10 mol of alkylene oxides.

As (meth)acrylate compounds mention may further be made of polyester (meth)acrylates, which are the (meth)acrylic esters or vinyl ethers of polyesterols, and also of urethane, epoxy or melamine (meth)acrylates.

Urethane (meth)acrylates, for example, are obtainable by reacting polyisocyanates with hydroxyalkyl(meth)acrylates and, where appropriate, chain extenders such as diols, polyols, diamines, polyamines, or dithiols or polythiols.

The urethane (meth)acrylates preferably have a number-average molar weight $M_n$ of from 500 to 20 000, in particular from 750 to 10 000, and more preferably from 750 to 3000 g/mol (as determined by gel permeation chromatography using polystyrene standards).

The urethane (meth)acrylates preferably contain from 1 to 5, more preferably from 2 to 4, mol of (meth)acrylic groups per 1000 g of urethane (meth)acrylate.

Epoxy (meth)acrylates are obtainable by reacting epoxides with (meth)acrylic acid. Examples of suitable epoxides include epoxidized olefins or glycidyl ethers, e.g. bisphenol A diglycidyl ether or aliphatic glycidyl ethers, such as butanediol diglycidyl ether.

Melamine (meth)acrylates are obtainable by reacting melamine with (meth)acrylic acid or the esters thereof.

The epoxy (meth)acrylates and melamine (meth)acrylates preferably have a number-average molar weight $M_n$ of from 500 to 20 000, more preferably from 750 to 10 000 g/mol and very preferably from 750 to 3000 g/mol; the amount of (meth)acrylic groups is preferably from 1 to 5, more preferably from 2 to 4, per 1000 g of epoxy (meth)acrylate or melamine (meth)acrylate (as determined by gel permeation chromatography using polystyrene standards and tetrahydrofuran as eluent).

Also suitable are carbonate (meth)acrylates, containing on average preferably from 1 to 5, in particular from 2 to 4, more preferably 2 or 3 (meth)acrylic groups and, with very particular preference, 2 (meth)acrylic groups.

The number-average molecular weight Mn of the carbonate (meth)acrylates is preferably less than 3000 g/mol, more preferably less than 1500 g/mol, very preferably less than 800 g/mol (as determined by gel permeation chromatography using polystyrene standards and tetrahydrofuran as solvent).

The carbonate (meth)acrylates are readily obtainable by transesterification of carbonic esters with polyhydric, preferably dihydric, alcohols (diols, e.g. hexanediol) and subsequent esterification of the free OH groups with (meth)acrylic acid or else transesterification with (meth)acrylic esters, as described for example in EP-A 92 269. They are also obtainable by reacting phosgene, urea derivatives with polyhydric alcohols, e.g. dihydric alcohols.

Suitable reactive diluents (compounds (H)) include radiation-curable, free-radically or cationically polymerizable compounds having only one ethylenically unsaturated copolymerizable group.

Examples that may be mentioned include $C_1$-$C_{20}$ alkyl (meth)acrylates, vinylaromatics having up to 20 carbon atoms, vinyl esters of carboxylic acids containing up to 20 carbon atoms, ethylenically unsaturated nitriles, vinyl ethers of alcohols containing 1 to 10 carbon atoms, α,β-unsaturated carboxylic acids and their anhydrides, and aliphatic hydrocarbons having from 2 to 8 carbon atoms and 1 or 2 double bonds.

Preferred alkyl(meth)acrylates are those with a $C_1$-$C_{10}$ alkyl radical, such as methyl methacrylate, methyl acrylate, n-butyl acrylate, ethyl acrylate, and 2-ethylhexyl acrylate.

In particular, mixtures of the alkyl(meth)acrylates are also suitable.

Examples of vinyl esters of carboxylic acids having 1 to 20 carbon atoms are vinyl laurate, vinyl stearate, vinyl propionate, and vinyl acetate.

Examples of α,β-unsaturated carboxylic acids and their anhydrides include acrylic acid, methacrylic acid, fumaric acid, crotonic acid, itaconic acid, maleic acid, and maleic anhydride, preferably acrylic acid.

Examples of suitable vinylaromatic compounds include vinyltoluene, α-butylstyrene, 4-n-butylstyrene, 4-n-decylstyrene, and, preferably, styrene.

Examples of nitriles are acrylonitrile and methacrylonitrile.

Examples of suitable vinyl ethers include vinyl methyl ether, vinyl isobutyl ether, vinyl hexyl ether, and vinyl octyl ether.

As nonaromatic hydrocarbons having 2 to 8 carbon atoms and one or two olefinic double bonds mention may be made of butadiene, isoprene, and of ethylene, propylene, and isobutylene.

It is further possible to employ N-vinylformamide, N-vinylpyrrolidone, and N-vinylcaprolactam.

As photoinitiator (I) it is possible to use photoinitiators known to the skilled worker, examples being those in "Advances in Polymer Science", Volume 14, Springer Berlin 1974 or in K. K. Dietliker, Chemistry and Technology of UV- and EB-Formulation for Coatings, Inks and Paints, Volume 3; Photoinitiators for Free Radical and Cationic Polymerization, P. K. T. Oldring (ed.), SITA Technology Ltd, London.

Suitable examples include mono- or bisacylphosphine oxides such as Irgacure 819 (bis(2,4,6-trimethylbenzoyl)phenylphosphine oxide), as described for example in EP-A 7 508, EP-A 57 474, DE-A 196 18 720, EP-A 495 751 or EP-A 615 980, examples being 2,4,6-trimethylbenzoyldiphenylphosphine oxide (Lucirin® TPO), ethyl 2,4,6-trimethylbenzoylphenylphosphinate, benzophenones, hydroxyacetophenones, phenylglyoxylic acid and derivatives thereof, or mixtures of these photoinitiators. Examples that may be mentioned include benzophenone, acetophenone, acetonaphthoquinone, methyl ethyl ketone, valerophenone, hexanophenone, α-phenyl-butyrophenone, p-morpholinopropiophenone, dibenzosuberone, 4-morpholinobenzophenone, 4-morpholinodeoxybenzoin, p-diacetylbenzene, 4-aminobenzophenone, 4'-methoxyacetophenone, β-methylanthraquinone, tert-butylanthraquinone, anthraquinonecarboxylic esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethylthioxanthone, 2,4-diethylthioxanthone, 2,4-diisopropylthioxanthone, 2,4-dichlorothioxanthone, benzoin, benzoin isobutyl ether, chloroxanthenone, benzoin tetrahydropyranyl ether, benzoin methyl ether, benzoin ethyl ether, benzoin butyl ether, benzoin isopropyl ether, 7H-benzoin methyl ether, benz[de]anthracen-7-one, 1-naphthaldehyde, 4,4'-bis(dimethylamino) benzophenone, 4-phenylbenzophenone, 4-chlorobenzophenone, Michler's ketone, 1-acetonaphthone, 2-acetonaphthone, 1-benzoylcyclohexan-1-ol, 2-hydroxy-2,2-dimethylacetophenone, 2,2-dimethoxy-2-phenylacetophenone, 2,2-diethoxy-2-phenylacetophenone, 1,1-dichloroacetophenone, 1-hydroxyacetophenone, acetophenone dimethyl ketal, o-methoxybenzophenone, triphenylphosphine, tri-o-tolylphosphine, benz[a]anthracene-7,12-dione, 2,2-diethoxyacetophenone, benzil ketals, such as benzil dimethyl ketal, 2-methyl-1-[4-(methylthio)phenyl]-2-morpholinopropan-1-one, anthraquinones such as 2-methylanthraquinone, 2-ethylanthraquinone, 2-tert-butylanthraquinone, 1-chloroanthraquinone, 2-amylanthraquinone, and 2,3-butanedione.

Also suitable are nonyellowing or low-yellowing photoinitiators of the phenylglyoxalic ester type, as described in DE-A 198 26 712, DE-A 199 13 353 or WO 98/33761.

Among said photoinitiators phosphine oxides, α-hydroxy ketones and benzophenones are preferred.

In particular it is also possible to use mixtures of different photoinitiators.

The photoinitiators can be used alone or in combination with a photopolymerization promoter, of the benzoic acid, amine or similar type, for example.

As further, typical coatings additives (J) it is possible to make use, for example, of antioxidants, oxidation inhibitors, stabilizers, activators (accelerators), fillers, pigments, dyes, devolatilizers, luster agents, antistats, flame retardants, thickeners, thixotropic agents, leveling assistants, binders, antifoams, fragrances, surfactants, viscosity modifiers, plasticizers, tackifying resins (tackifiers), chelating agents or compatibilizers.

Examples of accelerators for thermal aftercure that can be used include tin octoate, zinc octoate, dibutyltin laurate, and diazabicyclo[2.2.2]octane.

It is also possible to add one or more photochemically and/or thermally activatable initiators, such as potassium peroxodisulfate, dibenzoyl peroxide, cyclohexanone peroxide, di-tert-butyl peroxide, azobisisobutyronitrile, cyclohexylsulfonyl acetyl peroxide, diisopropyl percarbonate, tert-butyl peroctoate or benzpinacol, and also, for example, those thermally activatable initiators which have a half-life at 80° C. of more than 100 hours, such as di-t-butyl peroxide, cumene hydroperoxide, dicumyl peroxide, t-butyl perbenzoate, silylated pinacols, available commercially, for example, under the trade name ADDID 600 from Wacker, or hydroxyl-containing amine N-oxides, such as 2,2,6,6-tetramethylpiperidine-N-oxyl, 4-hydroxy-2,2,6,6-tetramethylpiperidine-N-oxyl etc.

Further examples of suitable initiators are described in "Polymer Handbook", 2nd ed., Wiley & Sons, New York.

Suitable thickeners besides free-radically (co)polymerized (co)polymers include customary organic and inorganic thickeners such as hydroxymethylcellulose or bentonites.

Examples of chelating agents which can be used include ethylenediamineacetic acid and salts thereof and also p-diketones.

Suitable fillers include silicates, examples being silicates obtainable by hydrolysis of silicon tetrachloride such as Aerosil® from Degussa, silicious earth, talc, aluminum silicates, magnesium silicates, calcium carbonates, etc.

Suitable stabilizers include typical UV absorbers such as oxanilides, triazines, and benzotriazole (the latter obtainable as Tinuvin® grades from Ciba-Spezialitatenchemie), and benzophenones. They can be used alone or together with suitable free-radical scavengers, examples being sterically hindered amines such as 2,2,6,6-tetramethylpiperidine, 2,6-di-tert-butylpiperidine or derivatives thereof, e.g., bis(2,2,6,6-tetramethyl-4-piperidyl) sebacate. Stabilizers are normally used in amounts of from 0.1 to 5.0% by weight, based on the solid components present in the formulation.

Examples of stabilizers which are additionally suitable include N-oxyls, such as 4-hydroxy-2,2,6,6-tetramethylpiperidine-N-oxyl, 4-oxo-2,2,6,6-tetramethylpiperidine-N-oxyl, 4-acetoxy-2,2,6,6-tetramethylpiperidine-N-oxyl, 2,2,6,6-tetramethylpiperidine-N-oxyl, 4,4',4''-tris(2,2,6,6-tetramethylpiperidine-N-oxyl) phosphite or 3-oxo-2,2,5,5- tetramethylpyrrolidine-N-oxyl, phenols and naphthols, such as p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (2,6-tert-butyl-p-cresol) or 4-tert-butyl-2,6-dimethylphenol, quinones, such as hydroquinone or hydroquinone monomethyl ether, aromatic amines, such as N,N-diphenylamine, N-nitrosodiphenylamine, phenylenediamines, such as N,N'-dialkyl-para-phenylenediamine, where the alkyl radicals can be identical or different, consist independently of 1 to 4 carbon atoms, and be straight-chain or branched, hydroxylamines, such as N,N-diethylhydroxylamine, urea derivatives, such as urea or thiourea, phosphorus compounds, such as triphenylphosphine, triphenyl phosphite or triethyl phosphite, or sulfur compounds, such as diphenyl sulfide or phenothiazine, for example.

Examples of typical compositions for radiation-curable materials are:
- (F) 20-100%, preferably 40-90%, more preferably 50-90%, and in particular 60-80% by weight,
- (G) 0-60%, preferably 5-50%, more preferably 10-40%, and in partcular 10-30% by weight,
- (H) 0-50%, preferably 5-40%, more preferably 6-30%, and in particular 10-30% by weight,
- (I) 0-20%, preferably 0.5-15%, more preferably 1-10%, and in partcular 2-5% by weight, and
- (J) 0-50%, preferably 2-40%, more preferably 3-30%, and in particular 5-20% by weight, with the proviso that (F), (G), (H), (I), and (J) together make 100% by weight.

The substrates are coated in accordance with methods which are conventional and are known to the skilled worker, applying at least one coating material to the target substrate in the desired thickness and removing any volatile constituents present in the coating material, with heating where appropriate. This operation can be repeated one or more times as desired. Application to the substrate may be made in a known way, for example, by spraying, troweling, knifecoating, brushing, rolling, roller coating, flow coating, laminating, injection backmolding or coextrusion. The coating thickness is generally in a range from about 3 to 1000 g/m$^2$ and preferably from 10 to 200 g/m$^2$.

Further disclosed is a method of coating substrates which comprises applying the coating material to the substrate and drying it where appropriate, curing it with electron beams or by UV exposure under an oxygenous atmosphere or, preferably, under inert gas, treating it thermally, if appropriate, at temperatures up to the level of the drying temperature, and then treating it thermally at temperatures of up to 160° C., preferably between 60 and 160° C.

The method of coating substrates may also be conducted by following the application of the coating material first with thermal treatment at temperatures of up to 160° C., preferably between 60 and 160° C., and then with curing using electron beams or by UV exposure under oxygen or, preferably, under inert gas.

Curing of the films formed on the substrate may take place by means of heat alone if desired. Generally, however, the coatings are cured both by exposure to high-energy radiation and thermally.

In addition to or instead of the thermal cure, curing may also take place by means of NIR radiation, which refers here to electromagnetic radiation in the wavelength range from 760 nm to 2.5 μm, preferably from 900 to 1500 nm.

Where two or more films of the coating composition are applied atop one another, it is possible for each coating operation to be followed by a thermal, NIR and/or radiation cure, if appropriate.

Examples of suitable radiation sources for the radiation cure include low-pressure, medium-pressure, and high-pressure mercury lamps, fluorescent tubes, pulsed lamps, metal halide lamps, electron flash installations, which allow radiation curing without photoinitiator, or excimer sources. Radiation curing is accomplished by exposure to high-energy radiation, i.e., UV radiation or daylight, preferably light in the wavelength (λ) range of from 200 to 700 nm, more preferably from 200 to 500 nm, and very preferably from 250 to 400 nm, or by bombardment with high-energy electrons (electron beams; 150 to 300 keV). Examples of radiation sources used include high-pressure mercury vapor lamps, lasers, pulsed lamps (flash light), halogen lamps, or excimer sources. The radiation dose normally sufficient for crosslinking in the case of UV curing is in the range from 80 to 3000 mJ/cm$^2$.

It is of course also possible to use two or more radiation sources for the cure, e.g., from two to four.

These sources may also each emit in different wavelength regions.

Irradiation can be carried out where appropriate in the absence of oxygen as well, such as under an inert gas atmosphere, for example. Suitable inert gases include, preferably, nitrogen, noble gases, carbon dioxide or combustion gases. Irradiation may also take place with the coating material covered with transparent media. Examples of transparent media include polymeric films, glass or liquids, such as water. Particular preference is given to irradiation in the manner described in DE-A1 199 57 900.

The invention further provides a method of coating substrates which comprises
- i) coating a substrate with a coating material as described above,
- ii) removing volatile constituents of the coating material, for the purpose of forming a film, under conditions in which the photoinitiator (I) essentially as yet does not form any free radicals,
- iii) if desired, irradiating the film formed in step ii) with high-energy radiation, the film being precured, and then, where appropriate, machining the article coated with the precured film or contacting the surface of the precured film with another substrate,
- iv) fully curing the film, thermally or with NIR radiation.

Steps iv) and iii) can also be carried out in reverse order, i.e., the film can be cured first thermally or by NIR radiation and then with high-energy radiation.

The present invention further provides substrates coated with a multicoat paint system of the invention.

The thickness of such a film to be cured as described can be from 0.1 μm up to several mm, preferably from 1 to 2000 μm, more preferably from 5 to 1000 μm, very preferably from 10 to 500 μm, and in particular from 10 to 250 μm.

In view of their relatively low coloring, the partial (meth) acrylic esters prepared in accordance with the invention can also be used with advantage in a thermally induced (free-radical) (co)polymerization.

Examples of monomers which may be copolymerized with the partial (meth)acrylic esters prepared in accordance with the invention include for example $C_1$-$C_{20}$ alkyl (meth)acrylates, vinylaromatics having up to 20 carbon atoms, vinyl esters of carboxylic acids comprising up to 20 carbon atoms, ethylenically unsaturated nitrites, vinyl ethers of alcohols comprising 1 to 10 carbon atoms, and aliphatic hydrocarbons having 2 to 8 carbon atoms and 1 or 2 double bonds.

Preferred (meth)acrylic acid alkyl esters are those with a $C_1$-$C_{10}$ alkyl radical, such as methyl methacrylate, methyl acrylate, n-butyl acrylate, ethyl acrylate and branched alkyl derivatives such as 2-ethylhexyl acrylate.

In particular, mixtures of the (meth)acrylic acid alkyl esters as well are suitable.

Vinyl esters of carboxylic acids having 1 to 20 carbon atoms are for example vinyl laurate, vinyl stearate, vinyl propionate and vinyl acetate.

Examples of suitable vinylaromatic compounds include vinyltoluene, α-butylstyrene, 4-n-butylstyrene, 4-n-decylstyrene and, preferably, styrene.

Examples of nitriles are acrylonitrile and methacrylonitrile.

Examples of suitable vinyl ethers are vinyl methyl ether, vinyl isobutyl ether, vinyl hexyl ether and vinyl octyl ether.

As nonaromatic hydrocarbons having 2 to 8 carbon atoms and one or two olefinic double bonds mention may be made of butadiene, isoprene, and also ethylene, propylene and isobutylene.

A frequent method, though not the only one, for preparing such (co)polymers is that of free-radical or ionic (co)polymerization in a solvent or diluent.

The free-radical (co)polymerization of such monomers takes place for example in aqueous solution in the presence of polymerization initiators which break down into free radicals under polymerization conditions, examples being peroxodisulfates, $H_2O_2$ redox systems or hydroxy peroxides, such as tert-butyl hydroperoxide or cumene hydroperoxide, for example. The (co)polymerization may be performed within a wide temperature range, where appropriate under reduced pressure or else under elevated pressure, generally at temperatures up to 100° C. The pH of the reaction mixture is commonly set in the range from 4 to 10.

Alternatively the (co)polymerization can be carried out in another way known per se to the skilled worker, continuously or batchwise, in the form for example of a solution, precipitation, water-in-oil emulsion, inverse emulsion, suspension or inverse suspension polymerization.

In the (co)polymerization the monomer/monomers is/are (co)polymerized using free-radical polymerization initiators, examples being azo compounds which break down into free radicals, such as 2,2'-azobis(isobutyronitrile), 2,2'-azobis(2-amidinopropane) hydrochloride or 4,4'-azobis(4'-cyanopentanoic acid) or dialkyl peroxides, such as di-tert-amyl peroxide, aryl alkyl peroxides, such as tert-butyl cumyl peroxide, alkyl acyl peroxides, such as tert-butyl peroxy-2-ethylhexanoate, peroxydicarbonates, such as di(4-tert-butylcyclohexyl) peroxydicarbonate, or hydroperoxides.

The stated compounds are generally used in the form of aqueous solutions or aqueous emulsions, the lower concentration being determined by the amount of water that is acceptable in the (co)polymerization and the upper concentration by the solubility of the respective compound in water.

Examples of compounds which can be used as solvents or diluents include water, alcohols, such as methanol, ethanol, n- or isopropanol, n- or isobutanol, or ketones, such as acetone, ethyl methyl ketone, diethyl ketone or isobutyl methyl ketone. Particular preference is given to nonpolar solvents such as, for example, xylene and its isomer mixtures, Shellsol® A and solvent naphtha.

In one preferred embodiment the monomers are premixed and initiator together if appropriate with further additions is added as a solvent solution. One particularly preferred embodiment is described in WO 01/23484, particularly therein on page 10, line 3 to line 24.

If appropriate the (co)polymerization can be conducted in the presence of polymerization regulators, such as hydroxylammonium salts, chlorinated hydrocarbons and thio compounds, such as tert-butyl mercaptan, thioglycolic acid ethylacrylic esters, mercaptoethanol, mercaptopropyltrimethoxysilane, dodecyl mercaptan, tert-dodecyl mercaptan or alkali metal hypophosphites, for example. In the (co)polymerization these regulators can be used, for example, in amounts of from 0 to 0.8 part by weight, based on 100 parts by weight of the monomers to be (co)polymerized, and they lower the molar mass of the resultant (co)polymer.

For emulsion polymerization it is possible to use dispersants, ionic and/or nonionic emulsifiers and/or protective colloids, and/or stabilizers, as surface-active compounds.

Suitable such compounds include not only the protective colloids that are normally used for implementing emulsion polymerizations, but also emulsifiers.

Examples of suitable protective colloids include polyvinyl alcohols, cellulose derivatives, and vinylpyrrolidone copolymers. An exhaustive description of further suitable protective colloids can be found in Houben-Weyl, Methoden der organischen Chemie, volume XIV/1, macromolecular compounds, Georg-Thieme-Verlag, Stuttgart, 1969, pp. 411 to 420. It will be appreciated that mixtures of emulsifiers and/or protective colloids can also be used. As dispersants it is preferred to use exclusively emulsifiers, whose relative molecular weights, unlike those of the protective colloids, are usually below 1000. They may be anionic, cationic or nonionic in nature. As will be appreciated it is necessary, when using mixtures of surface-active substances, that the individual components be compatible with one another, something which in case of doubt can be checked by means of a few preliminary tests. Generally speaking, anionic emulsifiers are compatible with one another and with nonionic emulsifiers.

The same also applies to cationic emulsifiers, whereas anionic and cationic emulsifiers are usually incompatible with one another. Examples of customary emulsifiers include ethoxylated mono-, di- and tri-alkylphenols (EO units: 3 to 100, alkyl: $C_4$ to $C_{12}$), ethoxylated fatty alcohols (EO units: 3 to 100, alkyl: $C_8$ to $C_{18}$), and also alkali metal and ammonium salts of alkyl sulfates (alkyl: $C_8$ to $C_{16}$) of sulfuric monoesters with ethoxylated alkylphenols (EO units: 3 to 100, alkyl: $C_4$ to $C_{12}$), of alkylsulfonic acids (alkyl: $C_{12}$ to $C_{18}$) and of alkylarylsulfonic acids (alkyl: $C_9$ to $C_{18}$). Further suitable emulsifiers, such as sulfosuccinic esters, can be found in Houben-Weyl, Methoden der organischen Chemie, volume XIV/1, macromolecular compounds, Georg-Thieme Verlag, Stuttgart, 1961, pages 192 to 208.

In general the amount of dispersant used is from 0.5 to 6%, preferably from 1 to 3% by weight, based on the monomers for free-radical polymerization.

Examples of (meth)acrylate-containing dispersions are n-butyl acrylate/acrylonitrile dispersions or n-butyl acrylate/butadiene/styrene dispersions which are employed as adhesives.

The polymer dispersions in which partial (meth)acrylic esters prepared in accordance with the invention are used may additionally be subjected to chemical and/or physical deodorization.

The copolymers obtainable with the partial (meth)acrylic esters prepared in accordance with the invention generally have a relatively low color number, which is advantageous in the coatings sector. The described copolymers can then be reacted in a manner known per se with amino resins, for example, such as melamine, to form crosslinked film-forming resins, as described for example in EP 738740 or EP 675141.

The coating materials of the invention are suitable with particular preference as or in exterior coatings, i.e., those applications which are exposed to daylight, preferably on buildings or parts of buildings, interior coatings, traffic markings, and coatings on vehicles and aircraft. The coatings are employed in particular as wood, paper or plastics coatings, for woodblock flooring or furniture for example.

The process of the invention allows the preparation of partial (meth)acrylic esters (F) in high chemical and space/time yield and under mild conditions and with good color numbers. Despite not using either protective groups or activated (meth)acrylic acid compounds, the desired partially esterified products are obtained in a targeted way, with high selectivity, and are free from by-products.

Where there are two or more lower-substituted hydroxyl groups present, then in general, if the amount of (meth)acrylating reagent is sufficient, all of the lower-substituted hydroxyl groups are substituted uniformly before higher-substituted hydroxyl groups are (meth)acrylated.

The selectivity of the reaction of the invention in respect of the (meth)acrylation of the hydroxyl groups having a lower degree of substituion as compared with the hydroxyl groups having a higher degree of substitution is generally at least 90:10, preferably at least 95:5, more preferably at least 97:3, very preferably at least 98:2, and in particular at least 99:1.

The fraction of multiply (meth)acrylated product is generally not more than 10 mol % based on the polyalcohol (C), preferably not more than 5 mol %, more preferably not more than 3 mol %, very preferably not more than 2 mol %, and in particular not more than 1 mol %.

The examples which follow are intended to illustrate the qualities of the invention without, however, restricting it.

EXAMPLES

Parts in this document, unless specified otherwise, are to be understood as referring to parts by weight.

Examples 1 and 2

DEOD Monoacrylate (with/without Solvent)

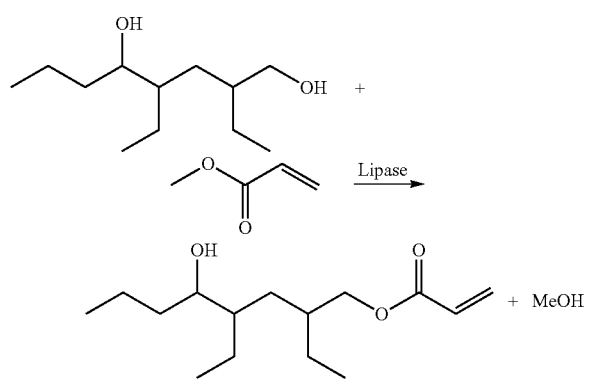

In a glass container with a screw-top lid, 5 mmol of 2,4-diethyloctane-1,5-diol (DEOD; 1.0 g) were shaken with 50 mmol of methyl acrylate (4.3 g), 50 mg of Novozym® 435 (supported lipase, Novozymes Denmark), optionally 5.0 ml of MTBE (tert-butyl methyl ether) and 1.0 g of 5 Å molecular sieve at 40° C. for 24 h.

Thereafter the solids were removed by filtration and a sample was silylated and analyzed by GC. The conversion of the diol to the monoacrylate was 96-98%. <0.5% of diacrylate was detected.

| Conditions | Conversion [%] |
| --- | --- |
| No solvent | 98 |
| MTBE | 96 |

Example 3

DEOD Monoacrylate (Preparative)

In a round-bottomed flask, 2.5 mol of 2,4-diethyloctane-1,5-diol (DEOD; 506 g) were stirred under reflux with 5.0 mol of methyl acrylate (431 g), 25 g of Novozym® 435 (supported lipase, Novozymes Denmark) and 750 g of 5 Å molecular sieve at 60° C. for 23 h. Thereafter the solids were removed by filtration and the product was washed with a little MTBE, and methyl acrylate and MTBE were removed under reduced pressure on a rotary evaporator.

This gave 406 g of a colorless liquid. A sample was silylated and analyzed by GC. The isolated product according to analysis contained 0.3% of 2,4-diethyloctane-1,5-diol and >99.5% of the product acrylated on the primary alcohol. <0.5% of diacrylate was detected.

Example 4

EHD Monoacrylate

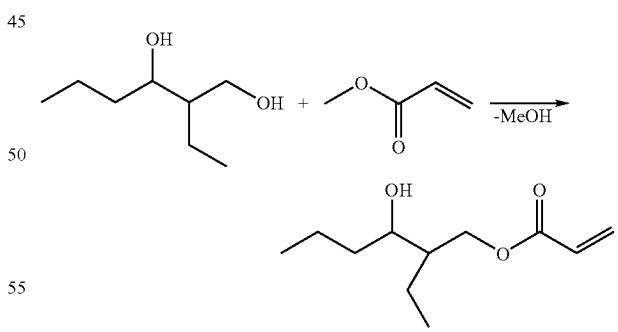

In a glass container with a screw-top lid, 5 mmol of 2-ethyl-1,3-hexanediol (EHD; 730 mg) were shaken with 50 mmol of methyl acrylate (4.3 g), 50 mg of Novozym® 435 (supported lipase, Novozymes Denmark) and 1.5 g of 5 Å molecular sieve at 60° C. for 8 h. Thereafter the solids were removed by filtration and a sample was silylated and analyzed by GC. The conversion of the diol to the monoacrylate was 98%. <0.5% of diacrylate was detected.

Example 5

DPPD Monoacrylate

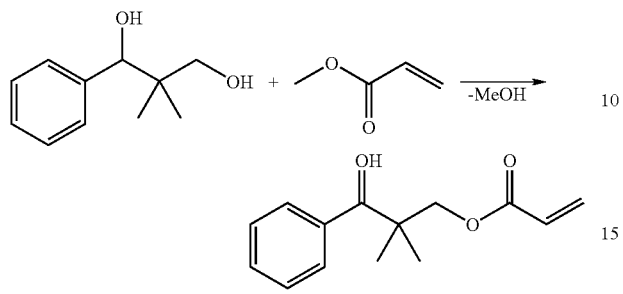

In a glass container with a screw-top lid, 5 mmol of 2,2-dimethyl-1-phenyl-1,3-propanediol (DPPD; 900 mg) were shaken with 50 mmol of methyl acrylate (4.3 g), 50 mg of Novozym® 435 (supported lipase, Novozymes Denmark) and 1.5 g of 5 Å molecular sieve at 40° C. for 8 h. Thereafter the solids were removed by filtration and a sample was silylated and analyzed by GC. The conversion of the diol to the monoacrylate was 99%. <0.5% of diacrylate was detected.

Example 6

DBD Monoacrylate

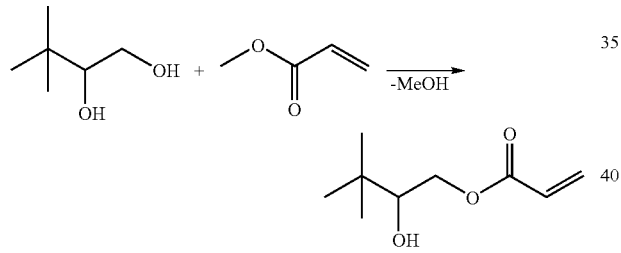

In a glass container with a screw-top lid, 5 mmol of 3,3-dimethyl-1,2-butanediol (DBD; 590 mg) were shaken with 50 mmol of methyl acrylate (4.3 g), 50 mg of Novozym® 435 (supported lipase, Novozymes Denmark) and 1.0 g of 5 Å molecular sieve at 40° C. for 24 h. Thereafter the solids were removed by filtration and a sample was silylated and analyzed by GC. The conversion of the diol to the monoacrylate was 97%. <0.5% of diacrylate was detected.

We claim:

1. A product obtained from an at least dihydric polyalcohol (C) comprising different hydroxyl groups by subjecting alternatively
    (1) at least one polyalcohol ($C_1$) having at least one primary hydroxyl group and at least one secondary hydroxyl group,
    or
    (2) at least one polyalcohol ($C_2$) having at least one primary hydroxyl group and at least one tertiary hydroxyl group,
    or
    (3) at least one polyalcohol ($C_3$) having at least one secondary hydroxyl group and at least one tertiary hydroxyl group, the more highly substituted hydroxyl group carrying in the β position at least one alkyl, cycloalkyl, aryl or aralkyl radical,
    or
    (4) at least one polyalcohol ($C_4$) having at least two primary hydroxyl groups, of which at least one carries in the β position at least one alkyl, cycloalkyl, aryl or aralkyl radical and at least one carries in the β position no such radical, or
    (5) at least one polyalcohol ($C_5$) having at least two secondary hydroxyl groups, of which at least one carries in the β position at least one alkyl, cycloalkyl, aryl or aralkyl radical and at least one carries in the β position no such radical,
    to esterification with (meth)acrylic acid or to transesterification with at least one (meth)acrylic ester (D) in the presence of at least one enzyme (E).

2. The product according to claim 1, which comprises a partial (meth)acrylic ester (F) of the formula Ia

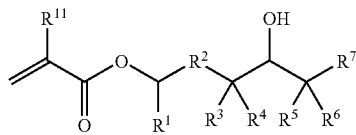

formula IIa

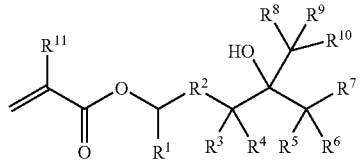

or formula IIIa

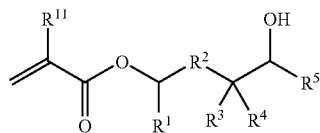

in which
$R^1$ and $R^3$ to $R^{10}$ each independently of one another are hydrogen, $C_1$-$C_{18}$ alkyl, $C_2$-$C_{18}$ alkyl optionally interrupted by one or more oxygen and/or sulfur atoms and/or one or more substituted or unsubstituted imino groups, or are $C_6$-$C_{12}$ aryl, $C_5$-$C_{12}$ cycloalkyl or a five- or six-membered, oxygen-, nitrogen- and/or sulfur-containing heterocycle, it being possible for the specified radicals to be substituted in each case by aryl, alkyl, aryloxy, alkyloxy, heteroatoms and/or heterocycles, and
$R^2$ is a single bond, $C_1$-$C_{20}$ alkylene, $C_5$-$C_{12}$ cycloalkylene, $C_6$-$C_{12}$ arylene or $C_2$-$C_{20}$ alkylene which is interrupted by one or more oxygen and/or sulfur atoms and/or one or more substituted or unsubstituted imino groups and/or one or more cycloalkyl, —(CO)—, —O(CO)O—, —(NH)(CO)O—, —O(CO)(NH)—, —O(CO)— or —(CO)O— groups, it being possible for the specified radicals to be substituted in each case by aryl, alkyl, aryloxy, alkyloxy, heteroatoms and/or heterocycles, and
$R^{11}$ is hydrogen or methyl.

3. The product according to claim 2, wherein the partial (meth)acrylic ester (F) is selected from the group consisting of 2-methyl-3-hydroxypentyl(meth)acrylate and 2,4-diethyl-1,5-dihydroxyoctyl(meth)acrylate.

4. The product according to claim 1, wherein polyalcohol $C_1$ is used.

5. The product according to claim 1, wherein polyalcohol $C_2$ is used.

6. The product according to claim 1, wherein polyalcohol $C_3$ is used.

7. The product according to claim 1, wherein polyalcohol $C_4$ is used.

8. The product according to claim 1, wherein polyalcohol $C_5$ is used.

9. The product according to claim 1, wherein the polyalcohol (C) is a polyalcohol of the formula I

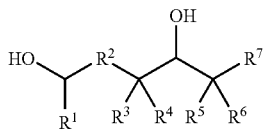

or formula II

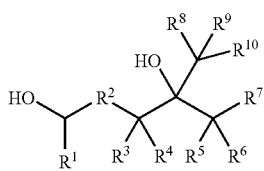

or formula III

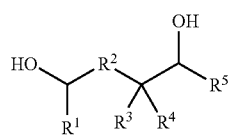

in which $R^1$ and $R^3$ to $R^{10}$ each independently of one another are hydrogen, $C_1$-$C_{18}$ alkyl, $C_2$-$C_{18}$ alkyl optionally interrupted by one or more oxygen and/or sulfur atoms and/or one or more substituted or unsubstituted imino groups, or are $C_6$-$C_{12}$ aryl, $C_5$-$C_{12}$ cycloalkyl or a five- or six-membered, oxygen-, nitrogen- and/or sulfur-containing heterocycle, it being possible for the specified radicals to be substituted in each case by aryl, alkyl, aryloxy, alkyloxy, heteroatoms and/or heterocycles, and $R^2$ is a single bond, $C_1$-$C_{20}$ alkylene, $C_5$-$C_{12}$ cycloalkylene, $C_6$-$C_{12}$ arylene or $C_2$-$C_{20}$ alkylene which is interrupted by one or more oxygen and/or sulfur atoms and/or one or more substituted or unsubstituted imino groups and/or one or more cycloalkyl, —(CO)—, —O(CO)O—, —(NH)(CO)O—, —O(CO)(NH)—, —O(CO)— or —(CO)O— groups, it being possible for the specified radicals to be substituted in each case by aryl, alkyl, aryloxy, alkyloxy, heteroatoms and/or heterocycles, where for the case (1) in claim 1 in formula I $R^1$ is hydrogen and at least one of the radicals $R^3$ to $R^7$ is other than hydrogen, for the case (2) in claim 1 in formula II $R^1$ is hydrogen and at least one of the radicals $R^3$ to $R^{10}$ is other than hydrogen, for the case (3) in claim 1 in formula II $R^1$ is other than hydrogen and at least one of the radicals $R^3$ to $R^{10}$ is other than hydrogen, for the case (4) in claim 1 in formula III $R^1$ and $R^5$ are hydrogen and at least one of the radicals $R^3$ and $R^4$ is other than hydrogen, and for the case (5) in claim 1 in formula III $R^1$ and $R^5$ are other than hydrogen and at least one of the radicals $R^3$ and $R^4$ is other than hydrogen.

10. The product according to claim 2, wherein the partial (meth)acrylic ester (F) has a color number below 100 APHA in accordance with DIN ISO 6271.

11. The product according to claim 10, wherein the color number is below 20 APHA.

* * * * *